(12) United States Patent
Laub

(10) Patent No.: US 12,064,510 B2
(45) Date of Patent: Aug. 20, 2024

(54) MEDICAL FOAM FOR DELIVERY OF AN ACTIVE AGENT

(71) Applicant: TDL Innovations, LLC, Princeton, NJ (US)

(72) Inventor: Glenn W. Laub, Princeton, NJ (US)

(73) Assignee: TDL INNOVATIONS, LLC, Princeton, NJ (US)

( * ) Notice: Subject to any disclaimer, the term of this patent is extended or adjusted under 35 U.S.C. 154(b) by 0 days.

(21) Appl. No.: 15/381,285

(22) Filed: Dec. 16, 2016

(65) Prior Publication Data

US 2018/0169012 A1 Jun. 21, 2018

(51) Int. Cl.
| | | |
|---|---|---|
| A61K 9/12 | (2006.01) | |
| A61K 47/02 | (2006.01) | |
| A61K 47/10 | (2017.01) | |
| A61K 47/36 | (2006.01) | |

(52) U.S. Cl.
CPC .............. *A61K 9/122* (2013.01); *A61K 47/02* (2013.01); *A61K 47/10* (2013.01); *A61K 47/36* (2013.01)

(58) Field of Classification Search
CPC ........ A61K 9/122; A61K 47/36; A61K 47/02; A61K 47/10
See application file for complete search history.

(56) References Cited

U.S. PATENT DOCUMENTS

| | | | |
|---|---|---|---|
| 2,190,688 A | 2/1940 | Snelling | |
| 2,569,683 A | 10/1951 | Lindsay | |
| 5,054,688 A | 10/1991 | Grindley | |
| 6,042,089 A * | 3/2000 | Klein | B01F 5/0403 261/76 |
| 6,103,695 A | 8/2000 | Lane et al. | |
| 6,187,290 B1 * | 2/2001 | Gilchrist | A61K 9/122 424/443 |
| 7,100,799 B2 * | 9/2006 | Gruenewald | A47J 43/121 222/1 |
| 8,198,365 B2 | 6/2012 | Ingenito et al. | |
| 8,445,589 B2 | 5/2013 | Ingenito et al. | |
| 8,501,230 B2 | 8/2013 | Alur et al. | |
| 8,691,278 B2 | 4/2014 | Alur et al. | |
| 2003/0152522 A1 * | 8/2003 | Miller | A61K 47/32 424/45 |
| 2004/0151774 A1 * | 8/2004 | Pauletti | A61K 9/0034 424/486 |
| 2008/0261884 A1 | 10/2008 | Tsai et al. | |
| 2008/0281433 A1 | 11/2008 | Chang et al. | |
| 2010/0075001 A1 * | 3/2010 | Succar | B65D 47/2018 426/115 |
| 2013/0046275 A1 | 2/2013 | Holzer et al. | |
| 2013/0131166 A1 | 5/2013 | Alur et al. | |
| 2013/0150883 A1 | 6/2013 | Fette et al. | |
| 2014/0369997 A1 * | 12/2014 | Grant | A61K 45/00 536/23.1 |
| 2015/0272883 A1 * | 10/2015 | Laub | A61K 33/18 424/400 |

FOREIGN PATENT DOCUMENTS

| | | | | |
|---|---|---|---|---|
| WO | WO-9515118 A1 * | 6/1995 | ............ | A61Q 19/00 |
| WO | 2009/073658 A1 | 6/2009 | | |
| WO | 2013/011504 A1 | 1/2013 | | |
| WO | 2015/153540 A2 | 10/2015 | | |

OTHER PUBLICATIONS

Yoshimura et al. ("Bronchial Blocker Lung Collapse Technique: Nitrous Oxide for Facilitating Lung Collapse During One-Lung Ventilation with a Bronchial Blocker," Anesthesia & Analgesia, Mar. 2014, vol. 118, No. 3, pp. 666-670) (Year: 2014).*
Eschwey et al. (WO9808523 translation) (Year: 1998).*
Terrado et al. (FR2997395A1 Machine Translation) (Year: 2014).*
Mondal, Pravakar, et al. "Evaluation of TRI-726 as a Drug Delivery Matrix," Drug Development and Industrial Pharmacy, 2011, 1-7.
Falkenstern-GE, R.F, et al. "Sever Emphysema Treated by Endoscopic Bronchial Volume Reduction with Lung Sealant (AeriSeal)," Hindawi Publishing Corp., Case Reports in Pulmonology, vol. 2013, Article ID 361391, 4 pages.
Oda, Shinchiro, et al. "Experimental Use of an Elastomeric Surgical Sealant for Arterial Hemostasis and its Long-Term Tissue Response," Interactive CardioVascular and Thoracic Surgery, vol. 10, 2010, 258-261.
Albanese, Giustino et al. "Pharmacology of Sclerotherapy," Seminars in Interventional Radiology, vol. 27, No. 4, 2010, 391-399.
Shiels, William, E., Presentation re: "New Concepts in Percutaneous MSK Treatment," ISSVA 2012, Malmo, Sweden, 37 pages.
Vaz, Marcelo Costa, et al. "Pleurodesis: Technique and Indications," J. Bras Pleumol, 2006: 32(4) 347-56.
Kennedy, L. et al., "Pleurodesis Using Talc Slurry," Chest, vol. 106, Issue 2, Aug. 1994, 342-346.

* cited by examiner

*Primary Examiner* — Robert A Wax
*Assistant Examiner* — Quanglong N Truong
(74) *Attorney, Agent, or Firm* — Fox Rothschild LLP

(57) ABSTRACT

A medical foam for delivering an active agent to a patient includes a biocompatible composition configured to form a foam, an active agent dissolved, dispersed, or suspended in the biocompatible composition, and a gas including nitrous oxide. The biocompatible composition may be configured to form a gel at a temperature of about 37° C. A method for administering an active agent to a patient includes preparing a mixture comprising a foamable liquid and the active agent, incorporating a gas comprising nitrous oxide into the mixture to create a foam containing the active agent, introducing the foam into a body cavity of the patient, and contacting the foam with a tissue surface in the body cavity.

15 Claims, No Drawings

MEDICAL FOAM FOR DELIVERY OF AN ACTIVE AGENT

FIELD OF THE INVENTION

The present invention, according to some embodiments, relates to compositions for delivering one or more active agents to a patient and methods of making and using the compositions. More particularly, the present invention in some embodiments relates to compositions for delivering one or more active agents to a body cavity, organ, or tissue of a patient. In some embodiments, the compositions are configured to form a gel. In some embodiments, the compositions are administered to the patient as a foam.

BACKGROUND OF THE INVENTION

During certain medical procedures, it is sometimes desirable or necessary to deliver an active agent directly to a body cavity, organ, or tissue of a patient. The active agent, for example, may be an active pharmaceutical ingredient (API), a hemostatic agent, a sealant, a thrombolytic agent, antiseptic agent, etc. The active agent may be dissolved or dispersed in a liquid which is then introduced directly to the target area of the patient, e.g., via a catheter.

Treatment success can be suboptimal, however, when the active agent is not effectively distributed to the target area or tissue. For instance, when the liquid containing the active agent is introduced into an organ or body cavity of the patient, the liquid will tend to collect at certain locations due to gravity which results in an uneven distribution of the active agent. In some cases, the liquid containing the active agent does not maintain sufficient contact with the target tissue to effectively deliver the active agent to the target tissue.

BRIEF SUMMARY OF THE INVENTION

The present invention according to certain embodiments provides a medical foam for delivering an active agent to a patient. In some embodiments, the medical foam includes a biocompatible composition configured to form a foam, a therapeutically effective amount of an active agent dissolved, dispersed, or suspended in the biocompatible composition, and a gas including nitrous oxide. The gas may be mixed, entrained, dissolved, or otherwise combined with the biocompatible composition to form a foam. In some embodiments, the volume of gas is greater than the volume of the biocompatible composition. In some embodiments, the gas includes at least 50% by volume of nitrous oxide. In some embodiments, the gas is a mixture of different gases (e.g., nitrous oxide and air). The active agent, in some embodiments, includes one or more agents selected from the group consisting of: thrombolytic agents, hemostatic agents, antiviral agents, cancer-treating agents, pleurodesis agents, vaccines, polypeptides, nucleotides, antiseptic agents, antibotic agents, tissue sealants, and bioadhesives. In some embodiments, the active agent may be included at about 0.1% to about 50% by weight of the biocompatible composition.

In some embodiments, the biocompatible composition is a foamable liquid, gel, or gel-forming composition. The biocompatible composition may be configured to form a foam when combined with the gas. In some embodiments, the biocompatible composition has a viscosity which increases in response to an increase in temperature. In some embodiments, the biocompatible composition includes one or more gel-forming polymers. In some embodiments, the biocompatible composition is configured to form a gel in response to an increase in temperature. In some embodiments, the biocompatible composition is configured to form a gel at a temperature of about human body temperature (about 37° C.). In some embodiments, the biocompatible composition comprises one or more copolymers of ethylene oxide and propylene oxide. In some embodiments, the biocompatible composition includes 10 wt % to 30 wt % of poloxamer in water. The poloxamer may be selected from the group consisting of Poloxamer 407 (F127), Poloxamer 338 (F108), Poloxamer 188 (F68), and combinations thereof. In some embodiments, the biocompatible composition additionally includes 1 wt % to 3 wt % xanthan gum or other compound configured to increase bioadhesiveness of the medical foam. In some embodiments, the biocompatible composition includes one or more of xanthan gum, locust bean, gum arabic, gum ghatti, guar gum, gum tragacanth, karaya gum, pullulan, alginate, carrageenan, pectin, gellan, chitosan, chondroitin sulfate, dermatin sulfate, and heparin. In further embodiments, the biocompatible composition additionally includes 1 wt % to 25 wt % polyethylene glycol (PEG), for example, PEG 200.

In some embodiments, a method for administering an active agent to a patient includes preparing a mixture comprising a foamable liquid and the active agent, incorporating a gas including nitrous oxide into the mixture to create a foam containing the active agent, introducing the foam into a body cavity of the patient, and contacting the foam with a tissue surface in the body cavity. The body cavity may include, for example, the pleural cavity, thoracic cavity, abdominal cavity, pelvic cavity, dorsal cavity, etc. The tissue surface may be, for example, an exterior surface of an organ, an interior surface of an organ, a surface of a mucous membrane, a surface of a blood vessel, a muscle tissue surface, cardiac tissue surface, pulmonary tissue surface, digestive tissue surface, bone tissue surface, tumor or other diseased tissue, etc.

In some embodiments, the gas includes at least 50% by volume of nitrous oxide. The active agent, in some embodiments, includes one or more agents selected from the group consisting of: thrombolytic agents, hemostatic agents, antiviral agents, cancer-treating agents, pleurodesis agents, vaccines, polypeptides, nucleotides, antiseptic agents, antibotic agents, tissue sealants, and bioadhesives. In some embodiments, the active agent may be included at about 0.1% to about 50% by weight of the foamable liquid.

In some embodiments, the foamable liquid comprises one or more copolymers of ethylene oxide and propylene oxide. In some embodiments, the foamable liquid comprises 10 wt % to 30 wt % of poloxamer in water. The poloxamer may be selected from the group consisting of Poloxamer 407 (F127), Poloxamer 338 (F108), Poloxamer 188 (F68), and combinations thereof. In some embodiments, the biocompatible composition additionally includes 1 wt % to 3 wt % xanthan gum or other compound configured to increase bioadhesiveness of the medical foam. In some embodiments, the biocompatible composition includes one or more of xanthan gum, locust bean, gum arabic, gum ghatti, guar gum, gum tragacanth, karaya gum, pullulan, alginate, carrageenan, pectin, gellan, chitosan, chondroitin sulfate, dermatin sulfate, and heparin. In further embodiments, the biocompatible composition additionally includes 1 wt % to 25 wt % polyethylene glycol (PEG).

In further embodiments of the method, the foamable liquid is configured to form a gel when introduced into the body cavity. In some embodiments, the foamable liquid is configured to form a gel at a temperature of about 37° C. In some embodiments, the method further includes storing the foamable liquid at a temperature below 25° C. prior to incorporating the gas into the mixture. In further embodiments, the mixture is stored in a container and the gas is stored in a pressurized cartridge, and incorporating the gas into the mixture includes releasing the gas from the pressurized cartridge into the container.

DETAILED DESCRIPTION

The present subject matter will now be described more fully hereinafter in which representative embodiments are described. The present subject matter can, however, be embodied in different forms and should not be construed as limited to the exemplary embodiments set forth herein. While certain embodiments are illustrative of compositions and methods that may be used for treatments of specific conditions (e.g., pleurodesis), the present invention is not intended to be limited to these uses. Indeed, other treatments may benefit from the advantages provided by the methods and compositions described herein.

The present invention, according to certain embodiments, generally includes methods and compositions for delivering one or more active agents to a patient. In some embodiments, the compositions are configured to deliver the one or more active agents to a body cavity, organ, or tissue surface of a patient. For example, in one embodiment, the methods and compositions of the present invention are particularly adapted for administering one or more active agents to the pleura of a patient. In some embodiments, for example, the methods and compositions described herein are useful for treating pleural effusions (e.g., malignant pleural effusions). In particular, certain embodiments of the invention relate to methods and compositions that are useful for pleurodesis. Such methods and compositions, for example, may be used to reduce or obliterate the pleural cavity of a patient to prevent fluid buildup in the pleural cavity.

Some embodiments of the present invention relate to preparing a composition including one or more active agents and introducing the composition into a body cavity and/or onto a tissue surface of the patient. In some embodiments, the compositions of the present invention include flowable compositions containing one or more active agents. In some embodiments, the compositions of the present invention are adapted to be introduced into a body cavity (e.g., the pleural cavity, thoracic cavity, abdominal cavity, pelvic cavity, dorsal cavity, etc.) of a patient, for example, via a catheter or a chest drain which may be inserted into the body cavity. In some embodiments, the compositions may be sprayed, injected or pumped into the target location in the patient's body. Access to the body cavity or target tissue may be obtained through surgical methods (e.g., open surgery, laparoscopic surgery, endoscopic surgery, etc.).

In some embodiments, the compositions of the present invention may include homogeneous mixtures or heterogeneous mixtures. In some embodiments, the compositions may include one or more liquid components which may be used to dissolve, suspend, disperse, or carry the one or more active agents. In some embodiments, the one or more liquid components are active agents. The liquid component may, for example, include liquid solutions, slurries, suspensions, or colloidal solutions. Moreover, the liquid component in some embodiments may include aqueous or non-aqueous liquids. In some embodiments, the liquid component is configured to undergo an increase in viscosity during and/or after introduction into the body of a patient. In some embodiments, the liquid component forms a mucoadhesive configured to adhere to a tissue surface of the patient. In some embodiments, the liquid component is or includes a gel, or a composition which is configured to form a gel (e.g., a hydrogel). In some embodiments, the one or more liquid components includes natural and/or synthetic polymers. In some embodiments, the liquid component is configured to form a gel after introduction into the body of a patient. In yet other embodiments, the liquid component is not a gel and/or does not form a gel (e.g., a hydrogel). In further embodiments, the compositions of the present invention may also include one or more components in a gaseous state. In some embodiments, the compositions include a gas or mixture of gases which may be admixed with the liquid component.

Compositions according to certain embodiments of the present invention include a foamable liquid as the liquid component. As used herein, the term foamable liquid refers to a liquid having the ability to form a foam. In some embodiments, the foamable liquid is configured to form a foam when the foamable liquid is admixed with a gas. As described herein, the foamable liquid may include, for example, liquid solutions, slurries, suspensions, or colloidal solutions. In other embodiments, the foamable liquid includes a gel or a composition which forms a gel (e.g., a hydrogel). In some embodiments, the foamable liquid includes one or more components configured to form a cross-linked polymer network, for example, during or after administration to a patient. In other embodiments, the foamable liquid is not or does not form a gel (e.g., a hydrogel) or a cross-linked polymer network. In some embodiments, the foamable liquid includes water. In some embodiments, the foamable liquid includes an aqueous solution, preferably an aqueous solution that can be absorbed by the patient's body without substantial adverse (e.g., toxic) effects. In some embodiments, the aqueous solution includes a saline solution. In some embodiments, the foamable liquid includes one or more of proteins, lipids, phospholipids, neutral lipids, and alcohols. In some embodiments, the liquid component is admixed with a gas to form a foam prior to administration to the patient, as will be described further herein. In other embodiments, the liquid component is configured to be administered to a patient in an unfoamed state and foamed within the patient's body (e.g., within a body cavity of the patient). In yet other embodiments, the liquid component is not foamed prior to administration to the patient.

Gases useful in the foamed compositions of the present invention preferably include gases that can be readily instilled into the body of the patient without substantial adverse (e.g., toxic) effects. In some embodiments, the gas is selected from the group consisting of air, nitrous oxide, carbon dioxide, oxygen, hydrogen, helium, argon, and mixtures thereof. Preferably, according to some embodiments, the gas is not pure nitrogen. In some embodiments, the gas includes nitrous oxide ($N_2O$) alone or in combination with one or more other gases (e.g., air, carbon dioxide, oxygen, hydrogen, helium, argon, etc.). In some embodiments, at least 10% of the gas by volume is nitrous oxide. In some embodiments, at least 15% of the gas by volume is nitrous oxide. In some embodiments, at least 20% of the gas by volume is nitrous oxide. In some embodiments, at least 25% of the gas by volume is nitrous oxide. In some embodiments, at least 30% of the gas by volume is nitrous oxide. In some embodiments, at least 35% of the gas by volume is nitrous oxide. In some embodiments, at least 40% of the gas by volume is nitrous oxide. In some embodiments, at least 45% of the gas by volume is nitrous oxide. In some embodiments, at least 50% of the gas by volume is nitrous oxide. In some embodiments, greater than 50% of the gas by volume is nitrous oxide. In some embodiments, at least 55% of the gas by volume is nitrous oxide. In some embodiments, at least 60% of the gas by volume is nitrous oxide. In some embodiments, at least 65% of the gas by volume is nitrous oxide. In some embodiments, at least 70% of the gas by volume is nitrous oxide. In some embodiments, at least 75% of the gas by volume is nitrous oxide. In some embodiments, at least 80% of the gas by volume is nitrous oxide. In some embodiments, at least 85% of the gas by volume is nitrous oxide. In some embodiments, at least 90% of the gas by volume is nitrous oxide. In some embodiments, at least 95% of the gas by volume is nitrous oxide. The remaining volume may be air or other gas as described herein.

In other embodiments, the gas includes one or more organic compounds. In some embodiments, the gas includes one or more hydrocarbons, for example, n-butane, n-pentane, or other saturated low boiling point aliphatic hydrocarbons. In further embodiments, the gas may include one or more fluorocarbons and/or hydrofluorocarbons. The organic compounds may be mixed with inorganic gases, e.g., nitrous oxide, helium, etc. Other aerosol spray propellants known in the art which do not have substantial adverse effects may also be used according to some embodiments. The gas in some embodiments includes vapors that may be, for example, produced from the evaporation or sublimation of a liquid or solid substance. In some embodiments, for example, the gas includes a volatile compound mixed with the foamable liquid and which causes the foamable liquid to foam as the volatile compound vaporizes. In some embodiments, the gas is generated from a chemical reaction, for example, an acid-base reaction. In some such embodiments, the foamable liquid may be or include a chemical reactant that reacts to produce a gas.

In further embodiments, the liquid component includes one or more surfactants. The one or more surfactants may include a biocompatible foaming agent selected to modify the stability of the foam formed when the foamable liquid is admixed with a gas. In some embodiments, the surfactants may further function as a sclerosing agent. In some embodiments, one or more surfactants includes sodium tetradecyl sulfate. Other surfactants that may be useful according to certain embodiments of the present invention include phospholipids, neutral lipids, hydrophobic surfactants, biocompatible soaps or detergents, and combinations thereof.

In some embodiments, the liquid component includes one or more polypeptides. In some embodiments, the liquid component includes one or more proteins. In some embodiments, the one or more proteins include an albumin (e.g., human serum albumin). Other proteins that may be used in the liquid component according to certain embodiments include surfactant associated proteins, for example, surfactant associated proteins B or C. In some embodiments, the one or more proteins includes only albumin. In other embodiments, the one or more proteins includes only surfactant associated proteins. In some embodiments, the one or more proteins includes a combination of albumin and a surfactant associated protein. In some embodiments, the albumin and/or other proteins included in the liquid component enhances the liquid component's ability to form a foam when the liquid component is admixed with a gas. In some embodiments, the one or more proteins (e.g., albumin) is present in the liquid component in an amount that is at least 0.5% by weight of the liquid component. In some embodiments, the one or more proteins (e.g., albumin) is present in the liquid component in an amount that is at least 1% by weight of the liquid component. In some embodiments, the one or more proteins (e.g., albumin) is present in the liquid component in an amount that is at least 5% by weight of the liquid component. In some embodiments, the one or more proteins (e.g., albumin) is present in the liquid component in an amount that is at least 10% by weight of the liquid component. In some embodiments, the one or more proteins (e.g., albumin) is present in the liquid component in an amount that is at least 15% by weight of the liquid component. In some embodiments, the one or more proteins (e.g., albumin) is present in the liquid component in an amount that is at least 20% by weight of the liquid component. In some embodiments, the one or more proteins (e.g., albumin) is present in the liquid component in an amount that is at least 25% by weight of the liquid component. In some embodiments, the one or more proteins (e.g., albumin) is present in the liquid component in an amount that is at least 30% by weight of the liquid component. In some embodiments, the one or more proteins (e.g., albumin) is present in the liquid component in an amount from about 1% to about 10% by weight of the liquid component. In some embodiments, the one or more proteins (e.g., albumin) is present in the liquid component in an amount from about 1% to about 20% by weight of the liquid component. In some embodiments, the one or more proteins (e.g., albumin) is present in the liquid component in an amount from about 1% to about 30% by weight of the liquid component. In some embodiments, the one or more proteins (e.g., albumin) is present in the liquid component in an amount from about 1% to about 40% by weight of the liquid component. In some embodiments, the one or more proteins (e.g., albumin) is present in the liquid component in an amount from about 1% to about 50% by weight of the liquid component. In some embodiments, the one or more proteins (e.g., albumin) is present in the liquid component in an amount from about 5% to about 25% by weight of the liquid component. In some embodiments, the one or more proteins (e.g., albumin) is present in the liquid component in an amount from about 10% to about 20% by weight of the liquid component. In some embodiments, the one or more proteins (e.g., albumin) is present in the liquid component in an amount no more than 50% by weight of the liquid component.

In some embodiments, a liquid component includes or consists of a biocompatible composition having a viscosity which increases during or after introduction into the body of the patient. In some embodiments, a liquid component includes or consists of a biocompatible composition having a viscosity which increases in response to an increase in temperature (e.g., from about room temperature to about human body temperature). In some embodiments, the liquid component includes a gel or a composition which forms a gel. In some embodiments, where the liquid component includes a gel or a composition which forms a gel, the liquid component may or may not also include one or more proteins (e.g., albumin or surfactant associated proteins), and may or may not include one or more surfactants as described above. In some embodiments, the gel or composition which forms a gel exhibits mucoadhesive properties. In some embodiments, the gel or composition which forms a gel exhibits mucoadhesive properties when or after being introduced into the body of a patient. In some embodiments, the gel or composition which forms a gel is configured to adhere to a surface of a tissue of the patient after administration to the target tissue. By adhering to a surface of the tissue, the composition may be able to more effectively deliver the active agent to the tissue by maintaining longer contact with the tissue. In some embodiments, the gel or composition which forms a gel includes or consists only of a biocompatible, biodegradable hydrogel. In some embodiments, the gel or composition which forms a gel includes one or more materials configured to form a gel during and/or after introduction into the patient (e.g., into the pleural cavity). In some embodiments, the gel or composition which forms a gel is configured to increase in viscosity after introduction into the patient such that, for example, the gel or composition which forms a gel can be introduced into the patient as a liquid and/or a foam. In some embodiments the gel or composition which forms a gel exhibits in situ reverse-thermal gelling. The gel or composition which forms a gel, in some embodiments, may be mixed with a gas component as described above (e.g., nitrous oxide) to form a foam before or during administration to the patient.

In some embodiments, the liquid component includes or consists of a gel, or a composition which forms a gel, that is substantially liquid (low viscosity) at about room temperature (e.g., about 20° C. to about 25° C.). In some embodiments, the viscosity of the gel or composition which forms a gel is less than 800,000 centipoise (cP) at about room temperature. In some embodiments, the viscosity of the gel or composition which forms a gel is less than 750,000 cP at about room temperature. In some embodiments, the viscosity of the gel or composition which forms a gel is less than 700,000 cP at about room temperature. In some embodiments, the viscosity of the gel or composition which forms a gel is less than 650,000 cP at about room temperature. In some embodiments, the viscosity of the gel or composition which forms a gel is less than 600,000 cP at about room temperature. In some embodiments, the viscosity of the gel or composition which forms a gel is less than 550,000 cP at about room temperature. In some embodiments, the viscosity of the gel or composition which forms a gel is less than 500,000 cP at about room temperature. In some embodiments, the viscosity of the gel or composition which forms a gel is less than 450,000 cP at about room temperature. In some embodiments, the viscosity of the gel or composition which forms a gel is less than 400,000 cP at about room temperature. In some embodiments, the viscosity of the gel or composition which forms a gel is less than 350,000 cP at about room temperature. In some embodiments, the viscosity of the gel or composition which forms a gel is less than 300,000 cP at about room temperature. In some embodiments, the viscosity of the gel or composition which forms a gel is less than 250,000 cP at about room temperature. In some embodiments, the viscosity of the gel or composition which forms a gel is less than 200,000 cP at about room temperature. In some embodiments, the viscosity of the gel or composition which forms a gel is less than 150,000 cP at about room temperature. In some embodiments, the viscosity of the gel or composition which forms a gel is less than 100,000 cP at about room temperature. In some embodiments, the viscosity of the gel or composition which forms a gel is less than 90,000 cP at about room temperature. In some embodiments, the viscosity of the gel or composition which forms a gel is less than 80,000 cP at about room temperature. In some embodiments, the viscosity of the gel or composition which forms a gel is less than 70,000 cP at about room temperature. In some embodiments, the viscosity of the gel or composition which forms a gel is less than 60,000 cP at about room temperature. In some embodiments, the viscosity of the gel or composition which forms a gel is less than 50,000 cP at about room temperature. In some embodiments, the viscosity of the gel or composition which forms a gel is less than 40,000 cP at about room temperature. In some embodiments, the viscosity of the gel or composition which forms a gel is less than 30,000 cP at about room temperature. In some embodiments, the viscosity of the gel or composition which forms a gel is less than 20,000 cP at about room temperature. In some embodiments, the viscosity of the gel or composition which forms a gel is less than 10,000 cP at about room temperature. In some embodiments, the viscosity of the gel or composition which forms a gel is less than 9,000 cP at about room temperature. In some embodiments, the viscosity of the gel or composition which forms a gel is less than 8,000 cP at about room temperature. In some embodiments, the viscosity of the gel or composition which forms a gel is less than 7,000 cP at about room temperature. In some embodiments, the viscosity of the gel or composition which forms a gel is less than 6,000 cP at about room temperature. In some embodiments, the viscosity of the gel or composition which forms a gel is less than 5,000 cP at about room temperature. In some embodiments, the viscosity of the gel or composition which forms a gel is less than 4,000 cP at about room temperature. In some embodiments, the viscosity of the gel or composition which forms a gel is less than 3,000 cP at about room temperature. In some embodiments, the viscosity of the gel or composition which forms a gel is less than 2,000 cP at about room temperature. In some embodiments, the viscosity of the gel or composition which forms a gel is less than 1,000 cP at about room temperature. In some embodiments, the viscosity of the gel or composition which forms a gel is less than 900 cP at about room temperature. In some embodiments, the viscosity of the gel or composition which forms a gel is less than 800 cP at about room temperature. In some embodiments, the viscosity of the gel or composition which forms a gel is less than 700 cP at about room temperature. In some embodiments, the viscosity of the gel or composition which forms a gel is less than 600 cP at about room temperature. In some embodiments, the viscosity of the gel or composition which forms a gel is less than 500 cP at about room temperature. In some embodiments, the viscosity of the gel or composition which forms a gel is less than 400 cP at about room temperature. In some embodiments, the viscosity of the gel or composition which forms a gel is less than 300 cP at about room temperature. In some embodiments, the viscosity of the gel or composition which forms a gel is less than 200 cP at about room temperature. In some embodiments, the viscosity of the gel or composition which forms a gel is less than 100 cP at about room temperature. In some embodiments, the viscosity of the gel or composition which forms a gel is less than 90 cP at about room temperature. In some embodiments, the viscosity of the gel or composition which forms a gel is less than 80 cP at about room temperature. In some embodiments, the viscosity of the gel or composition which forms a gel is less than 70 cP at about room temperature. In some embodiments, the viscosity of the gel or composition which forms a gel is less than 60 cP at about room temperature. In some embodiments, the viscosity of the gel or composition which forms a gel is less than 50 cP at about room temperature. In some embodiments, the viscosity of the gel or composition which forms a gel is less than 40 cP at about room temperature. In some embodiments, the viscosity of the gel or composition which forms a gel is less than 30 cP at about room temperature. In some embodiments, the viscosity of the gel or composition which forms a gel is less than 20 cP at about room temperature. In some embodiments, the viscosity of the gel or composition which forms a gel is less than 10 cP at about room temperature. In some embodiments, the viscosity of the gel or composition which forms a gel is less than 9 cP at about room temperature. In some embodiments, the viscosity of the gel or composition which forms a gel is less than 8 cP at about room temperature. In some embodiments, the viscosity of the gel or composition which forms a gel is less than 7 cP at about room temperature. In some embodiments, the viscosity of the gel or composition which forms a gel is less than 6 cP at about room temperature. In some embodiments, the viscosity of the gel or composition which forms a gel is less than 5 cP at about room temperature. In some embodiments, the viscosity of the gel or composition which forms a gel is less than 4 cP at about room temperature. In some embodiments, the viscosity of the gel or composition which forms a gel is less than 3 cP at about room temperature. In some embodiments, the viscosity of the gel or composition which forms a gel is less than 2 cP at about room temperature. In some embodiments, the viscosity of the gel or composition which forms a gel is less than 1 cP at about room temperature. In some embodiments, the viscosity of the gel or composition which forms a gel is less than 0.9 cP at about room temperature. In some embodiments, the viscosity of the gel or composition which forms a gel is less than 0.8 cP at about room temperature. In some embodiments, the viscosity of the gel or composition which forms a gel is less than 0.7 cP at about room temperature. In some embodiments, the viscosity of the gel or composition which forms a gel is less than 0.6 cP at about room temperature. In some embodiments, the viscosity of the gel or composition which forms a gel is less than 0.5 cP at about room temperature. In some embodiments, the viscosity of the gel or composition which forms a gel is less than 0.4 cP at about room temperature. In some embodiments, the viscosity of the gel or composition which forms a gel is less than 0.3 cP at about room temperature. In some embodiments, the viscosity of the gel or composition which forms a gel is less than 0.2 cP at about room temperature. In some embodiments, the viscosity of the gel or composition which forms a gel is less than 0.1 cP at about room temperature. In some embodiments, the viscosity of the gel or composition which forms a gel is between about 0.1 cP to about 1 cP at about room temperature. In some embodiments, the viscosity of the gel or composition which forms a gel is between about 0.1 cP to about 1.5 cP at about room temperature. In some embodiments, the viscosity of the gel or composition which forms a gel is between about 0.1 cP to about 2 cP at about room temperature. In some embodiments, the viscosity of the gel or composition which forms a gel is between about 0.1 cP to about 5 cP at about room temperature. In some embodiments, the viscosity of the gel or composition which forms a gel is between about 0.1 cP to about 10 cP at about room temperature. In some embodiments, the viscosity of the gel or composition which forms a gel is between about 1 cP to about 10 cP at about room temperature. In some embodiments, the viscosity of the gel or composition which forms a gel is between about 1 cP to about 50 cP at about room temperature. In some embodiments, the viscosity of the gel or composition which forms a gel is between about 1 cP to about 100 cP at about room temperature. In some embodiments, the viscosity of the gel or composition which forms a gel is between about 100 cP to about 200 cP at about room temperature. In some embodiments, the viscosity of the gel or composition which forms a gel is between about 100 cP to about 500 cP at about room temperature. In some embodiments, the viscosity of the gel or composition which forms a gel is between about 100 cP to about 1,000 cP at about room temperature. In some embodiments, the viscosity of the gel or composition which forms a gel is between about 1,000 cP to about 2,000 cP at about room temperature. In some embodiments, the viscosity of the gel or composition which forms a gel is between about 1,000 cP to about 5,000 cP at about room temperature. In some embodiments, the viscosity of the gel or composition which forms a gel is between about 1,000 cP to about 10,000 cP at about room temperature. In some embodiments, the viscosity of the gel or composition which forms a gel is between about 10,000 cP to about 20,000 cP at about room temperature. In some embodiments, the viscosity of the gel or composition which forms a gel is between about 10,000 cP to about 50,000 cP at about room temperature. In some embodiments, the viscosity of the gel or composition which forms a gel is between about 10,000 cP to about 100,000 cP at about room temperature. In some embodiments, the viscosity of the gel or composition which forms a gel is between about 10,000 cP to about 500,000 cP at about room temperature. In some embodiments, the viscosity of the gel or composition which forms a gel is between about 100,000 cP to about 150,000 cP at about room temperature. In some embodiments, the viscosity of the gel or composition which forms a gel is between about 100,000 cP to about 200,000 cP at about room temperature. In some embodiments, the viscosity of the gel or composition which forms a gel is between about 100,000 cP to about 250,000 cP at about room temperature. In some embodiments, the viscosity of the gel or composition which forms a gel is between about 100,000 cP to about 300,000 cP at about room temperature. In some embodiments, the viscosity of the gel or composition which forms a gel is between about 100,000 cP to about 350,000 cP at about room temperature. In some embodiments, the viscosity of the gel or composition which forms a gel is between about 100,000 cP to about 400,000 cP at about room temperature. In some embodiments, the viscosity of the gel or composition which forms a gel is between about 100,000 cP to about 450,000 cP at about room temperature. In some embodiments, the viscosity of the gel or composition which forms a gel is between about 100,000 cP to about 500,000 cP at about room temperature. In some embodiments, the viscosity of the gel or composition which forms a gel is between about 200,000 cP to about 300,000 cP at about room temperature. In some embodiments, the viscosity of the gel or composition which forms a gel is between about 200,000 cP to about 400,000 cP at about room temperature. In some embodiments, the viscosity of the gel or composition which forms a gel is between about 200,000 cP to about 500,000 cP at about room temperature. In some embodiments, the viscosity of the gel or composition which forms a gel is between about 300,000 cP to about 500,000 cP at about room temperature. In some embodiments, the viscosity of the gel or composition which forms a gel is between about 400,000 cP to about 500,000 cP at about room temperature. In some embodiments, the viscosity of the gel or composition which forms a gel is between about 400,000 cP to about 600,000 cP at about room temperature.

In some embodiments the liquid component includes or consists of a gel, or a composition which forms a gel, that is configured to undergo gellation at temperatures above room temperature. In some embodiments the gel or composition which forms a gel is configured to have a gelling temperature between 20° C. and 37° C. In some embodiments the gel or composition which forms a gel is configured to have a gelling temperature between 25° C. and 37° C. In some embodiments the gel or composition which forms a gel is configured to have a gelling temperature between 30° C. and 37° C. In some embodiments, the gel or composition which forms a gel may be stored or refrigerated below the gelling temperature prior to foaming or administration to the patient in order to prevent gellation. For example, the composition may be stored or refrigerated at 0° C. to 15° C. prior to foaming or administration. In some embodiments the gel or composition which forms a gel is configured to be in a solid or gelled state at human body temperature (about 37° C.). In some embodiments, the viscosity of the gel or composition which forms a gel is at least 10,000 cP at about human body temperature. In some embodiments, the viscosity of the gel or composition which forms a gel is at least 20,000 cP at about human body temperature. In some embodiments, the viscosity of the gel or composition which forms a gel is at least 30,000 cP at about human body temperature. In some embodiments, the viscosity of the gel or composition which forms a gel is at least 40,000 cP at about human body temperature. In some embodiments, the viscosity of the gel or composition which forms a gel is at least 50,000 cP at about human body temperature. In some embodiments, the viscosity of the gel or composition which forms a gel is at least 60,000 cP at about human body temperature. In some embodiments, the viscosity of the gel or composition which forms a gel is at least 70,000 cP at about human body temperature. In some embodiments, the viscosity of the gel or composition which forms a gel is at least 80,000 cP at about human body temperature. In some embodiments, the viscosity of the gel or composition which forms a gel is at least 90,000 cP at about human body temperature. In some embodiments, the viscosity of the gel or composition which forms a gel is at least 100,000 cP at about human body temperature. In some embodiments, the viscosity of the gel or composition which forms a gel is at least 150,000 cP at about human body temperature. In some embodiments, the viscosity of the gel or composition which forms a gel is at least 200,000 cP at about human body temperature. In some embodiments, the viscosity of the gel or composition which forms a gel is at least 250,000 cP at about human body temperature. In some embodiments, the viscosity of the gel or composition which forms a gel is at least 300,000 cP at about human body temperature. In some embodiments, the viscosity of the gel or composition which forms a gel is at least 350,000 cP at about human body temperature. In some embodiments, the viscosity of the gel or composition which forms a gel is at least 400,000 cP at about human body temperature. In some embodiments, the viscosity of the gel or composition which forms a gel is at least 450,000 cP at about human body temperature. In some embodiments, the viscosity of the gel or composition which forms a gel is at least 500,000 cP at about human body temperature. In some embodiments, the viscosity of the gel or composition which forms a gel is at least 550,000 cP at about human body temperature. In some embodiments, the viscosity of the gel or composition which forms a gel is at least 600,000 cP at about human body temperature. In some embodiments, the viscosity of the gel or composition which forms a gel is at least 650,000 cP at about human body temperature. In some embodiments, the viscosity of the gel or composition which forms a gel is at least 700,000 cP at about human body temperature. In some embodiments, the viscosity of the gel or composition which forms a gel is at least 750,000 cP at about human body temperature. In some embodiments, the viscosity of the gel or composition which forms a gel is at least 800,000 cP at about human body temperature. In some embodiments, the viscosity of the gel or composition which forms a gel is at least 850,000 cP at about human body temperature. In some embodiments, the viscosity of the gel or composition which forms a gel is at least 900,000 cP at about human body temperature. In some embodiments, the viscosity of the gel or composition which forms a gel is at least 950,000 cP at about human body temperature. In some embodiments, the viscosity of the gel or composition which forms a gel is at least 1,000,000 cP at about human body temperature. In some embodiments, the viscosity of the gel or composition which forms a gel is between about 50,000 cP to about 100,000 cP at about human body temperature. In some embodiments, the viscosity of the gel or composition which forms a gel is between about 100,000 cP to about 200,000 cP at about human body temperature. In some embodiments, the viscosity of the gel or composition which forms a gel is between about 200,000 cP to about 300,000 cP at about human body temperature. In some embodiments, the viscosity of the gel or composition which forms a gel is between about 300,000 cP to about 400,000 cP at about human body temperature. In some embodiments, the viscosity of the gel or composition which forms a gel is between about 400,000 cP to about 500,000 cP at about human body temperature. In some embodiments, the viscosity of the gel or composition which forms a gel is between about 500,000 cP to about 600,000 cP at about human body temperature. In some embodiments, the viscosity of the gel or composition which forms a gel is between about 500,000 cP to about 700,000 cP at about human body temperature. In some embodiments, the viscosity of the gel or composition which forms a gel is between about 500,000 cP to about 800,000 cP at about human body temperature. In some embodiments, the viscosity of the gel or composition which forms a gel is between about 500,000 cP to about 900,000 cP at about human body temperature. In some embodiments, the viscosity of the gel or composition which forms a gel is between about 500,000 cP to about 1,000,000 cP at about human body temperature. In some embodiments, the viscosity of the gel or composition which forms a gel is between about 600,000 cP to about 700,000 cP at about human body temperature. In some embodiments, the viscosity of the gel or composition which forms a gel is between about 600,000 cP to about 900,000 cP at about human body temperature. In some embodiments, the viscosity of the gel or composition which forms a gel is between about 600,000 cP to about 800,000 cP at about human body temperature. In some embodiments, the viscosity of the gel or composition which forms a gel is between about 600,000 cP to about 900,000 cP at about human body temperature. In some embodiments, the viscosity of the gel or composition which forms a gel is between about 600,000 cP to about 1,000,000 cP at about human body temperature. In some embodiments, the viscosity of the gel or composition which forms a gel is between about 700,000 cP to about 800,000 cP at about human body temperature. In some embodiments, the viscosity of the gel or composition which forms a gel is between about 700,000 cP to about 900,000 cP at about human body temperature. In some embodiments, the viscosity of the gel or composition which forms a gel is between about 700,000 cP to about 1,000,000 cP at about human body temperature. In some embodiments, the viscosity of the gel or composition which forms a gel is between about 800,000 cP to about 900,000 cP at about human body temperature. In some embodiments, the viscosity of the gel or composition which forms a gel is between about 800,000 cP to about 1,000,000 cP at about human body temperature. In some embodiments, the viscosity of the gel or composition which forms a gel is between about 900,000 cP to about 1,000,000 cP at about human body temperature.

In some embodiments, the viscosity of the gel or composition which forms a gel is configured to increase at least two to three times when transitioning from about room temperature to about human body temperature. In some embodiments, the viscosity of the gel or composition which forms a gel is configured to increase at least two to four times when transitioning from about room temperature to about human body temperature. In some embodiments, the viscosity of the gel or composition which forms a gel is configured to increase at least three to four times when transitioning from about room temperature to about human body temperature. In some embodiments, the viscosity of the gel or composition which forms a gel is configured to increase at least five times when transitioning from about room temperature to about human body temperature. In some embodiments, the viscosity of the gel or composition which forms a gel is configured to increase at least ten times when transitioning from about room temperature to about human body temperature. In some embodiments, the viscosity of the gel or composition which forms a gel is configured to increase at least a hundred times when transitioning from about room temperature to about human body temperature. In some embodiments, the viscosity of the gel or composition which forms a gel is configured to increase at least a thousand times when transitioning from about room temperature to about human body temperature. In some embodiments, the increased viscosity and/or mucoadhesive properties can be advantageous by increasing the contact time of the composition with the target tissue. Moreover, by having a lower viscosity when first introduced into the patient, the gel or composition which forms a gel can be more readily dispersed throughout the body cavity and better distributed over the surfaces of the target tissue before the composition forms a gel. The gel or composition which forms a gel, in some embodiments, may be mixed with a gas component as described above (e.g., nitrous oxide) to form a foam prior to and/or during administration to the patient.

The gel or composition which forms a gel according to some embodiments of the invention includes one or more polymers. In some embodiments, the gel or composition which forms a gel includes one or more synthetic polymers. In some embodiments, the gel or composition which forms a gel includes one or more tri-block copolymers. In some embodiments, the gel or composition which forms a gel includes one or more copolymers of ethylene oxide and propylene oxide. In some embodiments, the gel or composition which forms a gel includes one or more poloxamers (e.g., one or more poloxamers available under the trade names SYNPERONIC™ or PLURONIC®). In some embodiments, the gel or composition which forms a gel includes one or more polysaccharides. In some embodiments, the gel or composition which forms a gel includes xanthan gum. In some embodiments, the gel or composition which forms a gel includes a combination of one or more copolymers of ethylene oxide and propylene oxide and one or more polysaccharides. In some embodiments, the gel or composition which forms a gel includes a combination of one or more poloxamers and xanthan gum. In some embodiments, the xanthan gum may improve the bio-adhesiveness and/or gellation of the composition. Other compounds which may be included in the composition in addition to or instead of xanthan gum to improve bio-adhesiveness and/or gellation include: locust bean, gum arabic, gum ghatti, guar gum, gum tragacanth, karaya gum, pullulan, alginate, carrageenan, pectin, gellan, chitosan, chondroitin sulfate, dermatin sulfate, and heparin. In some embodiments, the gel or composition which forms a gel includes or consists of a combination of one or more poloxamers, xanthan gum, and water. In some embodiments, the gel or composition which forms a gel may further include polyethylene glycol (PEG). In some embodiments, the gel or composition which forms a gel includes or consists of a combination of one or more poloxamers and PEG. In some embodiments, the gel or composition which forms a gel includes or consists of a combination of one or more poloxamers, PEG, and water. In some embodiments, the PEG may be selected to have a relative molar mass ($M_r$) of 190 to 210. In some embodiments, the gel or composition which forms a gel includes biocompatible monomers which are configured to polymerize after introduction into the body of the patient (e.g., into the pleural cavity) to form a biocompatible gel. As discussed herein, the gel or composition which forms a gel may be mixed with a gas (e.g., nitrous oxide) to form a foam before or during the introduction into the body of the patient.

In some embodiments, the gel or composition which forms a gel includes or consists of, for example, one or more of the compositions described in U.S. Patent Application Publication No. US 2013/0131166, U.S. Pat. Nos. 8,501,230, 8,691,278, and International Application Publication No. WO 2009/073658, all of which are incorporated herein by reference in their entireties. In some embodiments, the gel or composition which forms a gel includes or consists of, for example, TRI-726 from TRILOGIC PHARMA described in Mondal, P. et al., "Evaluation of TRI-726 as a drug delivery matrix," *Drug Development and Industrial Pharmacy*, 2011, pp 1-7, which is incorporated herein by reference in its entirety. In some embodiments, the gel or composition which forms a gel includes or consists of, for example, 10 to 25 parts by weight of one or more poloxamers, 1 to 3 parts by weight of xanthan gum, and 72 to 89 parts by weight of water. In some embodiments, the gel or composition which forms a gel may further include polyethylene glycol. In some embodiments, a composition for delivering one or more active agents to a patient includes a mixture of 10 wt % to 30 wt % poloxamer in water. In some embodiments, a composition for delivering one or more active agents to a patient includes a mixture of 10 wt % to 30 wt % poloxamer and 1 wt % to 3 wt % xanthan gum in water. In some embodiments, a composition for delivering one or more active agents to a patient includes a mixture of 10 wt % to 30 wt % poloxamer and 1 wt % to 25 wt % polyethylene glycol in water. In some embodiments, a composition for delivering one or more active agents to a patient includes a mixture of 10 wt % to 30 wt % poloxamer, 1 wt % to 3 wt % xanthan gum, and 0 wt % to 25 wt % polyethylene glycol in water. In some embodiments, the mixtures may include one or more of the following in addition to or in place of xanthan gum: locust bean, gum arabic, gum ghatti, guar gum, gum tragacanth, karaya gum, pullulan, alginate, carrageenan, pectin, gellan, chitosan, chondroitin sulfate, dermatin sulfate, and heparin. Mixtures according to other embodiments may exclude xanthan gum and/or polyethylene glycol. In some embodiments, the mixtures include from 1 wt % to 3 wt % of one or more of xanthan gum, locust bean, gum arabic, gum ghatti, guar gum, gum tragacanth, karaya gum, pullulan, alginate, carrageenan, pectin, gellan, chitosan, chondroitin sulfate, dermatin sulfate, and heparin. In some embodiments, the mixture may be foamed with a gas (e.g., nitrous oxide, air, etc.) prior to or during administration to the patient.

In some embodiments, the poloxamer includes one or more poloxamers selected from the group consisting of Poloxamer 407 (F127), Poloxamer 338 (F108), and Poloxamer 188 (F68) available from BASF. In some embodiments, the one or more poloxamers includes or consists only of Poloxamer 407 (F127). In some embodiments, the one or more poloxamers includes or consists only of Poloxamer 338 (F108). In some embodiments, the one or more poloxamers includes or consists only of Poloxamer 188 (F68). In some embodiments, the one or more poloxamers includes or consists only of a mixture of Poloxamer 407 (F127) and Poloxamer 338 (F108). In some embodiments, the one or more poloxamers includes or consists only of a mixture of Poloxamer 407 (F127) and Poloxamer 188 (F68). In some embodiments, the one or more poloxamers includes or consists only of a mixture of Poloxamer 338 (F108) and Poloxamer 188 (F68). In some embodiments, the one or more poloxamers includes or consists only of a mixture of Poloxamer 407 (F127), Poloxamer 338 (F108) and Poloxamer 188 (F68). The "F" numbers provided in parentheses refers to the PLURONIC® trade name designations.

When the liquid components are admixed with a gas to form a foam in accordance with certain embodiments, the resulting foam will have a substantially greater volume in comparison to the volume of the unfoamed liquid component. This increase in volume is dependent on the amount of gas which is mixed with the liquid component for form the foam. Accordingly, in some embodiments, the amount of gas that is mixed with the liquid component may be selected based on the desired volume increase. For example in some embodiments, when the liquid component is foamed, the resulting composition is configured to have a volume that is about 1 to about 1000 times greater than the volume of the unfoamed liquid component. In some embodiments, the resulting composition has a volume that is about 1 to about 2 times greater than the volume of the unfoamed liquid component. In some embodiments, the resulting composition has a volume that is about 2 to about 3 times greater than the volume of the unfoamed liquid component. In some embodiments, the resulting composition has a volume that is about 3 to about 4 times greater than the volume of the unfoamed liquid component. In some embodiments, the resulting composition has a volume that is about 4 to about 5 times greater than the volume of the unfoamed liquid component. In some embodiments, the resulting composition has a volume that is about 5 to about 6 times greater than the volume of the unfoamed liquid component. In some embodiments, the resulting composition has a volume that is about 6 to about 7 times greater than the volume of the unfoamed liquid component. In some embodiments, the resulting composition has a volume that is about 7 to about 8 times greater than the volume of the unfoamed liquid component. In some embodiments, the resulting composition has a volume that is about 8 to about 9 times greater than the volume of the unfoamed liquid component. In some embodiments, the resulting composition has a volume that is about 9 to about 10 times greater than the volume of the unfoamed liquid component. In some embodiments, the resulting composition has a volume that is about 10 to about 20 times greater than the volume of the unfoamed liquid component. In some embodiments, the resulting composition has a volume that is about 20 to about 30 times greater than the volume of the unfoamed liquid component. In some embodiments, the resulting composition has a volume that is about 30 to about 40 times greater than the volume of the unfoamed liquid component. In some embodiments, the resulting composition has a volume that is about 40 to about 50 times greater than the volume of the unfoamed liquid component. In some embodiments, the resulting composition has a volume that is about 50 to about 60 times greater than the volume of the unfoamed liquid component. In some embodiments, the resulting composition has a volume that is about 60 to about 70 times greater than the volume of the unfoamed liquid component. In some embodiments, the resulting composition has a volume that is about 70 to about 80 times greater than the volume of the unfoamed liquid component. In some embodiments, the resulting composition has a volume that is about 80 to about 90 times greater than the volume of the unfoamed liquid component. In some embodiments, the resulting composition has a volume that is about 90 to about 100 times greater than the volume of the unfoamed liquid component. In some embodiments, the resulting composition has a volume that is about 100 to about 200 times greater than the volume of the unfoamed liquid component. In some embodiments, the resulting composition has a volume that is about 200 to about 300 times greater than the volume of the unfoamed liquid component. In some embodiments, the resulting composition has a volume that is about 300 to about 400 times greater than the volume of the unfoamed liquid component. In some embodiments, the resulting composition has a volume that is about 400 to about 500 times greater than the volume of the unfoamed liquid component. In some embodiments, the resulting composition has a volume that is about 500 to about 600 times greater than the volume of the unfoamed liquid component. In some embodiments, the resulting composition has a volume that is about 600 to about 700 times greater than the volume of the unfoamed liquid component. In some embodiments, the resulting composition has a volume that is about 700 to about 800 times greater than the volume of the unfoamed liquid component. In some embodiments, the resulting composition has a volume that is about 800 to about 900 times greater than the volume of the unfoamed liquid component. In some embodiments, the resulting composition has a volume that is about 900 to about 1000 times greater than the volume of the unfoamed liquid component. In some embodiments, the resulting composition has a volume that is at least 2 times greater than the volume of the unfoamed liquid component. In some embodiments, the resulting composition has a volume that is at least 5 times greater than the volume of the unfoamed liquid component. In some embodiments, the resulting composition has a volume that is at least 10 times greater than the volume of the unfoamed liquid component. In some embodiments, the resulting composition has a volume that is at least 20 times greater than the volume of the unfoamed liquid component. In some embodiments, the resulting composition has a volume that is at least 50 times greater than the volume of the unfoamed liquid component. In some embodiments, the resulting composition has a volume that is at least 100 times greater than the volume of the unfoamed liquid component. In some embodiments, the resulting composition has a volume that is at least 200 times greater than the volume of the unfoamed liquid component. In some embodiments, the resulting composition has a volume that is at least 500 times greater than the volume of the unfoamed liquid component. In some embodiments, the resulting composition has a volume that is at least 1000 times greater than the volume of the unfoamed liquid component.

The liquid component may be admixed with the gas to form a foam using any suitable technique known in the art. In some embodiments, the liquid component is agitated (e.g., shaken, whipped, or stirred) in the presence of the gas. In some embodiments, the gas is bubbled into the liquid component using a pump or pressurized gas source. In some embodiments, the gas and the liquid component are passed through a narrow orifice, for example, the orifice of a syringe. In some embodiments, the liquid component and the gas are contained at a pressure greater than atmospheric pressure (e.g., in a pressurized can) and foams as the liquid component and gas are released into atmospheric pressure. In some embodiments, the gas is dissolved in the liquid component under pressures greater than atmospheric pressure and expands as the as the liquid component and gas are released into atmospheric pressure to create a foam. In some embodiments, the gas and liquid components are contained in separate containers until just prior to or during administration to the patient. In some embodiments, the liquid component and the gas may be stored at different temperatures. In some embodiments, the liquid component is maintained at a temperature below room temperature (e.g., at temperatures from 0° C. to 20° C., 0° C. to 15° C., 0° C. to 10° C., or 0° C. to 5° C.) until use. In some embodiments, the liquid component may be stored and dispensed from a dispensing container to which a removable/replaceable cartridge or canister of pressurized gas (e.g., pressurized nitrous oxide) may be attached and used to pressurize the container. In some embodiments, the gas forms a foam with the liquid component as the gas and liquid component are dispensed from the container. In one such example, a dispensing container may be utilized similar to the configurations described in U.S. Pat. No. 2,190,688 or U.S. Pat. No. 7,100,799, which are incorporated herein by reference in their entirety. In some embodiments, the container outlet may be further attached to a catheter such that the foam is delivered from the container to the patient through the catheter. Preferably the container, catheter, and any other equipment that contacts the liquid component should be sterile. In other embodiments, the liquid component and gas are admixed and introduced using an injector, ejector, eductor-jet pump, aspirator pump, or other device using a Venturi effect. Examples of such devices are described in U.S. Pat. Nos. 2,569,683, 5,054,688, and 6,042,089, which are each incorporated herein by reference in their entirety. In some embodiments, a predetermined amount of gas is admixed with the liquid component. Preferably the gas and liquid component are mixed until at least the desired volume of foam is produced.

In some embodiments, the foam comprises bubbles of the gas having a size range of about 0.1 mm to about 20 mm in diameter. In some embodiments, the foam comprises bubbles of the gas having a size range of about 0.5 mm to about 15 mm in diameter. In some embodiments, the foam comprises bubbles of the gas having a size range of about 1 mm to about 10 mm in diameter. In some embodiments, the foam comprises bubbles of the gas having an average diameter ranging from about 1 mm to about 20 mm. In some embodiments, the foam comprises bubbles of the gas having an average diameter ranging from about 1 mm to about 15 mm. In some embodiments, the foam comprises bubbles of the gas having an average diameter ranging from about 1 mm to about 10 mm. In other embodiments, the average diameter of the bubbles of gas does not exceed 15 mm in diameter. In some embodiments, the average diameter of the bubbles of gas does not exceed 10 mm in diameter. In some embodiments, the average diameter of the bubbles of gas does not exceed 5 mm in diameter. In some embodiments, the average diameter of the bubbles of gas does not exceed 2 mm in diameter. In some embodiments the average diameter of the bubbles of gas does not exceed 1 mm in diameter.

As described, the active agent(s) useful in the compositions of the present invention may be dissolved, dispersed, suspended, or carried by the liquid component. In some embodiments, the active agent(s) are dissolved, dispersed, suspended, or carried by the liquid component prior to foaming the liquid component. In other embodiments, the active agent(s) are added to the liquid component after the liquid component has been foamed. In some embodiments, the liquid component by itself is an active agent (e.g., capable of inducing a biological response). In some embodiments, the active agent may include one or more of pharmaceuticals, thrombolytic agents, hemostatic agents, antiviral agents, cancer-treating agents, vaccines, polypeptides, nucleotides, antiseptic agents, tissue sealants, and antibotic agents. In some embodiments, active agents useful in embodiments of the present invention are particularly adapted for use in chemical pleurodesis. In some embodiments, the one or more active agents may be selected from any agent known in the art to be useful in chemical pleurodesis. In some embodiments, the one or more active agents includes a sclerosing agent. In some embodiments, the active agents are selected to cause irritation, inflammation, fibrosis, and/or scarring of the patient's pleura when introduced into the pleural cavity of the patient. For example, in some embodiments, the active agents include one or more agents selected from the following: doxycycline, bleomycin, tetracycline, povidone iodine, talc, silica (e.g., fumed silica), and quinacrine. In some embodiments, the active agents include a chemotherapy agent, an antibiotic, or combinations thereof. Other active agents that may be suitable for use in compositions according to embodiments of the present invention are described in U.S. Pat. No. 6,103,695, which is incorporated herein by reference in its entirety.

In some further embodiments, compositions according to the present invention include at least one active agent that is an adhesive substance. In some such embodiments, the active agent may be configured to adhere layers of tissue together, for example, the layers of the patient's pleura. In some such embodiments, the adhesive substance is capable of permanently adhering the layers of the pleura together. In some embodiments, the adhesive substance includes a hemostatic sealant. In some embodiments, the adhesive substance includes a fibrin- or collagen-based tissue adhesive. In some embodiments, the adhesive substance includes one or more of fibrin sealants, gelatin-resorcin-aldehydes (e.g., gelatin-resorcin-formaldehyde/glutaraldehyde glues), protein-aldehyde systems, polysaccharide-based adhesives, mussel adhesive proteins, and biomimetic glues. In some embodiments, the adhesive substance includes one or more cyanoacrylate adhesives. The adhesive substance may be the only active agent or included in combination with other active agents, for example, an active agent configured to cause irritation, inflammation, fibrosis, and/or scarring of the patient's pleura as described above.

Compositions according to some embodiments of the present invention are not necessarily limited to use in pleurodesis. Other conditions that affect the pleura or pleural cavity of a patient may also be treated according to certain methods and compositions of the present invention. In some embodiments, for example, compositions of the present invention may be useful in administering one or more active agents for treating infections or bleeding in the pleural cavity, penumothorax, or hemothorax. According to some of these embodiments, the compositions include one or more active agents selected from antibiotics, sealants, hemostatic agents, and lytic agents. In other embodiments, the compositions include one or more agents capable of reducing fluid formation or fluid leakage into the pleural cavity. In some embodiments, the compositions include one or more agents capable of increasing fluid reabsorption. Other active agents that can be administered by methods and compositions of the present invention include cancer-treating agents, nucleotides, vaccines, biopharmaceuticals, and therapeutic proteins or polypeptides.

The one or more active agents are preferably present in the composition in a therapeutically effective amount. The therapeutically effective amount should be an amount of the active agent that is capable of achieving a desired physiological effect when administered to the patient. When used for pleurodesis, for example, the one or more active agents are preferably present in a therapeutically effective amount sufficient to cause fusion of the patient's pleura. In some embodiments, the one or more active agents are present in the composition from trace amounts to about 0.1% by weight of the liquid component. In some embodiments, the one or more active agents are present in the composition from 0.001% to about 0.1% by weight of the liquid component. In some embodiments, the one or more active agents are present in the composition from 0.01% to about 0.1% by weight of the liquid component. In some embodiments, the one or more active agents are present in the composition from 0.02% to about 0.1% by weight of the liquid component. In some embodiments, the one or more active agents are present in the composition from 0.03% to about 0.1% by weight of the liquid component. In some embodiments, the one or more active agents are present in the composition from 0.04% to about 0.1% by weight of the liquid component. In some embodiments, the one or more active agents are present in the composition from 0.05% to about 0.1% by weight of the liquid component. In some embodiments, the one or more active agents are present in the composition from 0.06% to about 0.1% by weight of the liquid component. In some embodiments, the one or more active agents are present in the composition from 0.07% to about 0.1% by weight of the liquid component. In some embodiments, the one or more active agents are present in the composition from 0.08% to about 0.1% by weight of the liquid component. In some embodiments, the one or more active agents are present in the composition from 0.09% to about 0.1% by weight of the liquid component. In some embodiments, the one or more active agents are present in the composition in an amount that is at least 0.1% by weight of the liquid component. In some embodiments, the one or more active agents are present in the composition in an amount that is at least 0.5% by weight of the liquid component. In some embodiments, the one or more active agents are present in the composition in an amount that is at least 1% by weight of the liquid component. In some embodiments, the one or more active agents are present in the composition in an amount that is at least 2% by weight of the liquid component. In some embodiments, the one or more active agents are present in the composition in an amount that is at least 5% by weight of the liquid component. In some embodiments, the one or more active agents are present in the composition in an amount that is at least 10% by weight of the liquid component. In some embodiments, the one or more active agents are present in the composition in an amount that is at least 15% by weight of the liquid component. In some embodiments, the one or more active agents are present in the composition in an amount that is at least 20% by weight of the liquid component. In some embodiments, the one or more active agents are present in the composition in an amount from about 0.1% to about 50% by weight of the liquid component. In some embodiments, the one or more active agents are present in the composition in an amount from about 0.1% to about 40% by weight of the liquid component. In some embodiments, the one or more active agents are present in the composition in an amount from about 0.1% to about 30% by weight of the liquid component. In some embodiments, the one or more active agents are present in the composition in an amount from about 0.1% to about 25% by weight of the liquid component. In some embodiments, the one or more active agents are present in the composition in an amount from about 0.1% to about 20% by weight of the liquid component. In some embodiments, the one or more active agents are present in the composition in an amount from about 0.1% to about 15% by weight of the liquid component. In some embodiments, the one or more active agents are present in the composition in an amount from about 0.1% to about 10% by weight of the liquid component. In some embodiments, the one or more active agents are present in the composition in an amount from about 0.1% to about 9% by weight of the liquid component. In some embodiments, the one or more active agents are present in the composition in an amount from about 0.1% to about 8% by weight of the liquid component. In some embodiments, the one or more active agents are present in the composition in an amount from about 0.1% to about 7% by weight of the liquid component. In some embodiments, the one or more active agents are present in the composition in an amount from about 0.1% to about 6% by weight of the liquid component. In some embodiments, the one or more active agents are present in the composition in an amount from about 0.1% to about 5% by weight of the liquid component. In some embodiments, the one or more active agents are present in the composition from about 0.1% to about 4% by weight of the liquid component. In some embodiments, the one or more active agents are present in the composition from about 0.1% to about 3% by weight of the liquid component. In some embodiments, the one or more active agents are present in the composition from about 0.1% to about 2% by weight of the liquid component. In some embodiments, the one or more active agents are present in the composition from about 0.1% to about 1% by weight of the liquid component. In some embodiments, the one or more active agents are present in the composition at less than 1% by weight of the liquid component. In other embodiments, the one or more active agents are present in the composition in an amount greater than 50% by weight of the liquid component, e.g., from 50% to 60% by weight of the liquid component, from 60% to 70% by weight of the liquid component, from 70% to 80% by weight of the liquid component, from 80% to 90% by weight of the liquid component, or from 90% to 99% by weight of the liquid component. In certain embodiments, the liquid component by itself is an active agent, for example, capable to cause irritation, inflammation, fibrosis, and/or scarring of the patient's pleura as described without the use of additional active agents. According to some of these embodiments, the amount of active agent present in the composition would be equal to the weight of the liquid component.

The compositions according to certain embodiments of the invention can be introduced into the body of the patient using any suitable technique known in the art for introducing a fluid into the patient's body. When used for pleurodesis, for example, techniques used to introduce chemical agents during typical chemical pleurodesis procedures can also be used to introduce compositions of the present invention into the pleural cavity. In some embodiments, for example, the composition can be introduced into the pleural cavity via a catheter or chest drain that is inserted into the pleural cavity. In some embodiments, the compositions may be injected into the pleural cavity of the patient. In some embodiments, the pleural cavity is first drained or aspirated of any effusions or other fluids prior to introducing the composition. In some embodiments, the composition can be introduced during open surgery wherein the pleural cavity is directly accessible. In some embodiments, for example, the composition may be sprayed, poured, or otherwise directly introduced into the patient's body. In other embodiments, the composition can be introduced during laparoscopic, videoscopic, or robotic surgery via minimally invasive techniques.

In some embodiments, the compositions are introduced into the patient's body as a foam after the liquid component has been admixed with a gas. In other embodiments, the composition is introduced into the patient's body before the liquid component is admixed with a gas. According to these embodiments, the liquid component may then foamed within the patient's body by mixing the liquid component with a gas. In yet other embodiments, the liquid component is foamed as it is introduced into the patient's body. For example, in some embodiments, both the liquid component and a gas may be combined together as the components are introduced into the patient's body. As described, for example, in some embodiments the liquid component and the gas are contained at a pressure greater than atmospheric pressure (e.g., in a pressurized can) and foams as the liquid component and gas are released into the lower pressure of the patient's body. In some embodiments, the foam is delivered into the patient's body via a catheter that is positioned at or proximate to the target tissue, organ, or body cavity. In other embodiments, the liquid component and gas are admixed and introduced into the pleural cavity using an injector, ejector, eductor-jet pump, aspirator pump, or other device using a Venturi effect.

In a foamed state, the compositions according to some embodiments of the present invention may provide particular advantages for delivering the one or more active agents to the patient. For example, foaming may improve contact between the active agent that is dissolved, dispersed, suspended or carried in the foam and the target tissue since it may not drain away as rapidly. Improving contact between the active agent and the target tissue can also reduce the total amount of active agent needed since it is more effectively delivered to the patient. These and other advantages may result from the increase in volume caused by foaming the liquid component which, for example, allows greater distribution the one or more active agents throughout the target area. Moreover, in some embodiments, foaming may improve adherence of the composition with the tissue surface thereby increasing contact between the pleura and the active agent.

In some embodiments, the total volume of foam produced is between about 1 mL to about 100 mL. In some embodiments, the total volume of foam produced is between about 1 mL to about 10 mL. In some embodiments, the total volume of foam produced is between about 1 mL to about 2 mL, between about 2 mL to about 3 mL, between about 3 mL to about 4 mL, between about 4 mL to about 5 mL, between about 5 mL to about 6 mL, between about 6 mL to about 7 mL, between about 7 mL to about 8 mL, between about 8 mL to about 9 mL, or between about 9 mL to about 10 mL. In some embodiments, the total volume of foam produced is between about 10 mL to about 100 mL. In some embodiments, the total volume of foam produced is between about 10 mL to about 20 mL, between about 20 mL to about 30 mL, between about 30 mL to about 40 mL, between about 40 mL to about 50 mL, between about 50 mL to about 60 mL, between about 60 mL to about 70 mL, between about 70 mL to about 80 mL, between about 80 mL to about 90 mL, or between about 90 mL to about 100 mL. In some embodiments, the total volume of foam produced is between about 50 mL to about 100 mL. In some embodiments, the total volume of foam produced is between about 75 mL to about 100 mL. In some embodiments, the total volume of foam produced is between about 100 mL to about 200 mL, between about 200 mL to about 300 mL, between about 300 mL to about 400 mL, between about 400 mL to about 500 mL, between about 500 mL to about 600 mL, between about 600 mL to about 700 mL, between about 700 mL to about 800 mL, between about 800 mL to about 900 mL, or between about 900 mL to about 1000 mL. In some embodiments, the total volume of foam produced is at least 100 mL. In some embodiments, the total volume of foam produced is at least 200 mL. In some embodiments, the total volume of the foam produced is at least 500 mL. In some embodiments, the total volume of the foam produced is at least 750 mL. In some embodiments, the total volume of the foam produced is at least 1000 mL. In some embodiments, the total volume of the foam produced is between about 500 mL to about 1000 mL. In some embodiments, the total volume of the foam produced is between about 750 mL to about 1000 mL. In some embodiments, the total volume of the foam produced is between about 1000 mL to about 1500 mL. In some embodiments, the total volume of the foam produced is between about 1500 mL to about 2000 mL.

In some embodiments, the total amount of the one or more active agents to be introduced into the patient's body may range from about 100 mg to about 20 g, depending on the type of active agent used and the tissue being treated. For example in pleurodesis, when talc is used as the active agent, the total amount of talc included in the composition may range from about 1 g to about 15 g, 2 g to about 12 g, from about 2.5 g to about 10 g, from about 3 g to about 7 g, or from about 4 g to about 6 g, according to some embodiments. In other embodiments, where the active agent is doxycycline, bleomycin, tetracycline, quinacrine or combinations thereof, the total amount of active agent included in the composition may range, for example, from about 50 mg to about 2000 mg, about 100 mg to about 1000 mg, about 200 mg to about 800 mg, from about 300 mg to about 700 mg, or from about 400 mg to about 600 mg. Other active agents may be included in lesser or greater amounts.

In certain embodiments, after the composition is introduced into the patient's body (e.g., in the pleural cavity), the foam is allowed to contact a surface of the target tissue. In some embodiments, contacting the tissue with the foam exposes the tissue to the one or more active agents that are dissolved, suspended, dispersed, and/or carried by the foam. As described above and herein, in some embodiments the foam allows greater distribution of the one or more active agents throughout the target area (e.g., the pleural cavity in pleurodesis). For example, in some embodiments the volume of foam introduced into the patient's body may be sufficient to fill substantially the entire target area such that substantially all of target tissue is exposed to the one or more active agents. Accordingly, certain embodiments of the present invention may avoid the problem faced during typical procedures wherein the active agent collects at certain locations in the body cavity resulting in an uneven distribution of the active agent and incomplete treatment. Moreover, in some embodiments, the foam may improve adherence of the composition with the tissue thereby increasing contact between the tissue and the one or more active agents.

In some embodiments particularly, the foam is preferably allowed to contact the target tissue for at least an amount of time sufficient for the active agent to act on the target tissue and/or be absorbed by the target tissue. In some embodiments, when used for pleurodesis for example, the foam is preferably allowed to contact the pleura for at least an amount of time sufficient for the active agent to initiate inflammation and/or adhesion of the pleural layers. In some embodiments, the desired contact time is at least 1 minute, at least 2 minutes, at least 5 minutes, at least 10 minutes, at least 15 minutes, at least 30 minutes, at least 45 minutes, or at least 60 minutes. In some embodiments, the desired contact time ranges from about 1 hour to about 24 hours, from about 2 hours to about 20 hours, from about 4 hours to about 18 hours, from about 6 hours to about 16 hours, from about 8 hours to about 14 hours, or from about 10 hours to about 12 hours.

In some embodiments, the foam may be allowed to remain within and absorbed by the patient's body. Absorption may occur over a period of one to seven days according to some embodiments. For example, in some embodiments, the foam is formulated to dissipate over time and the remaining residual liquid absorbed by the patient's body. In other embodiments, the residual liquid or a portion thereof is drained from the patient after or while the foam dissipates. Dissipation of the foam refers to the gas escaping from the foam. In some embodiments, the foam is configured to dissipate within 1 hour, within 2 hours, within 4 hours, within 8 hours, within 12 hours, or within 24 hours. In some embodiments, the foam is configured to begin dissipation immediately after formation and/or administration to the patient. In some embodiments, the foam is configured to begin dissipation in less than a minute after formation and/or administration to the patient. In some embodiments, the foam is configured to dissipate in less than 1 hour, e.g., between 0 minutes to 60 minutes.

In other embodiments, the compositions of the present invention are actively removed from the patient's body after the desired amount of contact time has occurred. For example, in some embodiments, the foam introduced into the patient's body is removed from the patient's body after 5 minutes, after 30 minutes, after 1 hour, after 12 hours, after 24 hours, etc. In some embodiments, the foam is removed before 24 hours. It should be understood that removal of the composition from the patient's body may leave residual amounts of the composition and active agent(s) in the patient's body. Therefore removal of the compositions refers to removal of at least a portion of the compositions. In some embodiments, the composition may be actively removed from the patient's body using any techniques known in the art for removing fluid from the patient's body. In some embodiments, removal is carried out using one or more of aspirating, draining, and intubation. In some embodiments, at least a portion of the composition is passively drained from the patient's body by gravity. In other embodiments, at least a portion of the composition is pumped from the patient's body. In some embodiments, at least a portion of the foam is allowed to dissipate prior to removal from the patient's body. The gas released from the dissipated foam may be allowed to be absorbed by the patient's body or removed, e.g., by draining or aspirating the pleural cavity.

In certain embodiments of the invention, the foamed composition may be configured to form a gel which can preferably adhere to the target tissue to deliver the active agent. Some such embodiments may be achieved where the liquid component includes or consists of a gel, or a composition which forms a gel (e.g., hydrogel), as described above. For example, the liquid component may include or consist of a combination of one or more poloxamers, xanthan gum, polyethylene gycol, water, and one or more active agents. In some embodiments, the composition is delivered into the patient's body as a foam (e.g., after combining with nitrous oxide and/or other gas) and is configured to form a gel in response to the body temperature of the patient. In some embodiments, the composition forms a gel after some or all of the gas has dissipated from the foam. In other embodiments, the composition forms a gel while in a foamed state. In some embodiments, the gel is configured to release the active agent over time (e.g., over a period of 1 to 10 days). Preferably the one or more active agents are mixed with the gel or composition which forms a gel prior to introduction into the patient. In some embodiments, the gel or a composition which forms a gel and the one or more active agents are introduced into the patient simultaneously. In other embodiments, the one or more active agents are introduced into the patient after the gel or a composition which forms a gel is introduced into the patient. In some embodiments, the gel is actively removed from the patient after a predetermined time. In other embodiments, the gel is configured to biodegrade and be absorbed by the patient's body. In some embodiments, the gel is configured to remain in the patient from about 1 to about 10 days. Preferably, when used for pleurodesis, the gel is configured to remain in the patient for at least a period of time sufficient for the active agent(s) to cause fusion of the pleura.

In other embodiments, the gel or composition which forms a gel is not admixed with gas to form a foam. Instead, according to some these embodiments, the gel or composition which forms a gel may be introduced into the patient in a substantially liquid (low viscosity) state and allowed to form a gel within the patient without foaming. The gel or composition which forms a gel may be introduced into the patient as a liquid via a catheter, spray, injection, or other suitable technique known in the art and allowed to form a gel inside the patient's body. As the gel is formed, the gel contacts and adheres to the target tissue and exposes the tissue to the active agent(s). The example gels or compositions which form gels described above may be used in this manner according to some embodiments of the invention.

In some embodiments relating to pleurodesis, fusion of the inner and outer pleurae is achieved as a result of one or more active agents triggering fibrosis or the formation scar tissue between the inner and outer pleurae. In other embodiments, where the active agent is an adhesive substance, fusion of the pleural layers is achieved by adhering the layers together with the adhesive substance. In some embodiments, fusion of the pleural layers may occur within one to several days after treatment with the compositions of present invention. In preferred embodiments, the pleural cavity is obliterated as a result of the fusion of the pleural layers. In some embodiments, the volume of the pleural cavity is reduced to at least an extent sufficient to prevent or minimize any pleural effusions.

While certain embodiments described herein relate particularly to pleurodesis, it should be understood that the compositions of the present invention may be used in other medical procedures according to further embodiments. Accordingly, the foams and other compositions described herein may be used in additional embodiments to deliver one or more active agents to other body cavities (thoracic cavity, abdominal cavity, pelvic cavity, dorsal cavity, etc.), organs, tissues, or mucous membranes. For example, the foams and compositions described herein may also be used to contact tumor tissues and deliver cancer-treating drugs as the active agent, deliver tissue sealants to cut or lacerated tissues, deliver antiseptic and/or antibiotic agents throughout a body cavity during surgery, etc. Moreover, while certain example active agents have been described which may be delivered by the foams and compositions of the present invention, it should be appreciated that other active agents could also be delivered using the foams and compositions of the present invention.

It should be understood that various changes, substitutions, and alterations can be made herein without departing from the spirit and scope of the invention as defined by the appended claims. It should also be apparent that individual elements identified herein as belonging to a particular embodiment may be included in other embodiments of the invention. Moreover, the scope of the present application is not intended to be limited to the particular embodiments of the process, machine, manufacture, and composition of matter, means, methods and steps described in the specification. As one of ordinary skill in the art will readily appreciate from the disclosure herein, processes, machines, manufacture, composition of matter, means, methods, or steps, presently existing that perform substantially the same function or achieve substantially the same result as the corresponding embodiments described herein may be utilized according to the present invention.

What is claimed is:

1. A method for administering an active agent to a body cavity of patient in need thereof comprising:
    preparing a mixture comprising a foamable liquid and the active agent;
    dissolving a gas comprising nitrous oxide into the mixture under pressures greater than atmospheric pressure to create a medical foaming composition containing the active agent that forms a foam upon exposure to the lower pressure in the patient's body cavity;
    introducing the medical foaming composition into a body cavity of the patient; and
    contacting the medical foaming composition with a tissue surface in the body cavity, wherein the medical foaming composition is formulated to adhere to the tissue surface and deliver the active agent to the tissue surface.

2. The method of claim 1, wherein the foamable liquid is configured to form a gel at a temperature of about 37° C.

3. The method of claim 1, wherein the foamable liquid comprises one or more copolymers of ethylene oxide and propylene oxide.

4. The method of claim 1, wherein the foamable liquid comprises 10 wt % to 30 wt % of poloxamer in water.

5. The method of claim 4, wherein the poloxamer is selected from the group consisting of Poloxamer 407, Poloxamer 338, Poloxamer 188, and combinations thereof.

6. The method of claim 4, wherein the foamable liquid further comprises one or more of xanthan gum, locust bean, gum arabic, gum ghatti, guar gum, gum tragacanth, karaya gum, pullulan, alginate, carrageenan, pectin, gellan, chitosan, chondroitin sulfate, dermatin sulfate, and heparin.

7. The method of claim 4, wherein the foamable liquid further comprises 1 wt % to 25 wt % polyethylene glycol.

8. The method of claim 4, wherein the foamable liquid includes a composition configured to form a gel when introduced into the body cavity.

9. The method of claim 1, wherein the gas comprises at least 50% by volume of nitrous oxide.

10. The method of claim 1, wherein the active agent includes one or more agents selected from the group consisting of: thrombolytic agents, hemostatic agents, antiviral agents, cancer-treating agents, pleurodesis agents, vaccines, polypeptides, nucleotides, antiseptic agents, antibiotic agents, tissue sealants, and bioadhesives.

11. The method of claim 1, further comprising storing the foamable liquid at a temperature below 25° C. prior to incorporating the gas into the mixture.

12. The method of claim 1, wherein the mixture is stored in a container and the gas is stored in a pressurized cartridge, and wherein dissolving the gas into the mixture comprises releasing the gas from the pressurized cartridge into the container.

13. The method of claim 1, wherein the active agent is an antiseptic agent.

14. The method of claim 1 wherein, the body cavity is a cavity selected from the group consisting of a thoracic cavity, an abdominal cavity, a pelvic cavity, and a dorsal cavity of the patient.

15. The method of claim 14, wherein the thoracic cavity is the pleural cavity.

* * * * *